United States Patent [19]

Bøler et al.

[11] 4,175,084

[45] Nov. 20, 1979

[54] COUPLING PRODUCTS OF BIOLOGICALLY ACTIVE AMINES

[75] Inventors: Jan B. Bøler; Karl-Ludvig Reichelt, both of Oslo, Norway

[73] Assignee: Sentralinstitutt for Industriell Forskning, Oslo, Norway

[21] Appl. No.: 810,471

[22] Filed: Jun. 27, 1977

[30] Foreign Application Priority Data

Jun. 25, 1976 [NO] Norway ............................ 762199

[51] Int. Cl.$^2$ .......................................... C07D 207/40
[52] U.S. Cl. ........................... 260/326.44; 260/326.43; 260/326.14 R; 546/226; 546/245; 562/448

[58] Field of Search ...................... 260/326.44, 326.43

[56] References Cited

U.S. PATENT DOCUMENTS 3,903,077   9/1975   Jones et al. .................... 260/326.47

*Primary Examiner*—Donald G. Daus
*Assistant Examiner*—Mary Lee
*Attorney, Agent, or Firm*—Wenderoth, Lind & Ponack

[57] ABSTRACT

The invention relates to physiologically active compounds which are coupling products between an N-acyl aspartic acid and a biologically active amine such as dopamine or serotonin.

4 Claims, No Drawings

COUPLING PRODUCTS OF BIOLOGICALLY ACTIVE AMINES

Biologically active amines play an active role in normal brain function and are expected in the future to be of therapeutic value in the treatment of several types of disorders. As an example, deficiency of dopamine (DA) is observed in Parkinson's disease, and normalisation of the dopamine level may restore normal conditions. Further, hyper-activity of DA in the limbic part of the brain is the most likely cause of acute psychoses. Thus, amphetamine leads to such psychoses and is an agonist (stimulator) of the DA receptor, and most antipsychotic agents (psychosolytic agents) act by hampering the receptor for the DA-dependant 3,5-AMP-production. Here, normal conditions can also be restored by increasing the amount of competing amines, such as serotonin 5-hydroxytryptamine, 5HT) or noradrenalin (NA).

Further, the learning can possibly by influenced directly. There are numerous data indicating that the 5HT system is connected to the "punishing" and catecholamines to the "rewarding" system of the brain. It would be of importance in the behaviour therapy to facilitate the learning of desired patterns of behaviour and inhibit the undesired ones (which bother the patient).

However, it is a problem to transport said biologically active amines to the locality where they are to exert their activity.

If for instance dopamine (dihydroxyphenyl-ethylamine) is administered intravenously, orally etc., the dopamine seems not to cross the blood-brain barrier. Instead, its immediate biological precursor, L-dopa (dihydroxyphenyl-alanine) which can cross said barrier, is administered. However, large amounts of L-dopa will be decarboxylated peripherally, and consequently high doses of L-dopa must be given to maintain a sufficiently high blood concentration. Therapeutically, however, it is not desired to administer large amounts of L-dopa, particularly because of undesired side effects. These problems have partly been overcome by the addition of decarboxylase-inhibitors through preparations containing L-dopa. More L-dopa will thereby reach the brain and be converted therein to dopamine. These same principles which are illustrated above for dopamine/L-dopa may also be valid for other biologically active amines.

In general, the aromatic amines have been far better investigated than the aliphatic ones. Partly, one has not been able to get the latter into the brain experimentally, and partly has the lack of sufficiently sensitive analytical techniques made it impossible to study these amines in situ to the same extent as the aromatic ones.

It has now been found that it is possible to transport the biologically active amine into the brain by bonding it chemically to a N-acyl-aspartic acid of the formula

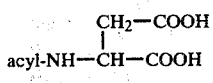

wherein "acyl" has the formula $C_xH_{2x+1}CO$, in which x is an integer from 0 to 17, particularly 0 or 1.

Thus, the acylated acid is used as a carrier which brings the desired amine to the place of action where the amine is liberated and exerts it activity. The acid is normally present in the brain, and a minor increase in this amount should usually not disturb normal body function.

This principle can be used for several amines. As an example, piperidine is related to sleep, and piperidine which is amide-bonded to N-acetyl-aspartic acid (NAA) will possibly be a suitable sleeping agent due to better transport to the central nervous system (CNS).

Serotonin is inter alia involved in the mechanism of sleep, hyperactivity syndrome in children and together with dopamine in learning. Hyperactivity syndrome is today treated with for instance amphetamine. If NAA-5HT or -DA can be taken up directly, it will be possible to attain a more specific treatment.

In connection with research it is also very important to bring to the brain such amines as phenyl ethyl amine, octopamine, tryptamine and tyramine, which are all possible signal transmitters and for which direct uptake is excluded due to the blood-brain barrier. Further the situation is that NAA, when coupled to monoamine, more easily enters the CNS, which makes it possible to tag the NAA-pool and thereby the compounds (peptides) which are formed from this substance (inter alia releasing hormones).

U.S. Pat. No. 3,676,492 relates to amino acid amides of the formula

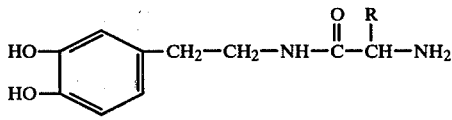

wherein R inter alia may be carboxymethyl (i.e. dihydroxyphenyl-ethyl-aspartylamide) but this meaning has not been illustrated, and it has not been explained at all how amides of dibasic acids should be prepared, and N-acylated acids are also not mentioned and are not comprised by the formula of the patent.

From Norwegian Patent Application No. 74,1143 (priority from U.S.A. application Ser. No. 348,440 of Apr. 5, 1973, now U.S. Pat. No. 3,903,077) it is known to prepare similar amino acid amides of dopamine by reacting an activated ester of a suitable N-carbobenzyloxy amino acid with dopamine or a salt thereof, whereafter the N-carbobenzyloxy group is split off. Aspartic acid is mentioned as a possible acid, but there is no example of either this or other dibasic acids, or of N-acylated acids.

1. According to the invention the dibasic aspartic acid may be bonded chemically to the biologically active amine in several different ways:
 (A) at the α-carboxyl group
 (B) at the β-carboxyl group
 (C) at both carboxyl groups (diamide)
 (D) through the cyclic imide form:

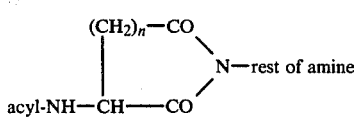

Form D applies to primary amines only.

With dopamine as an example these types of coupling may be illustrated as follows:

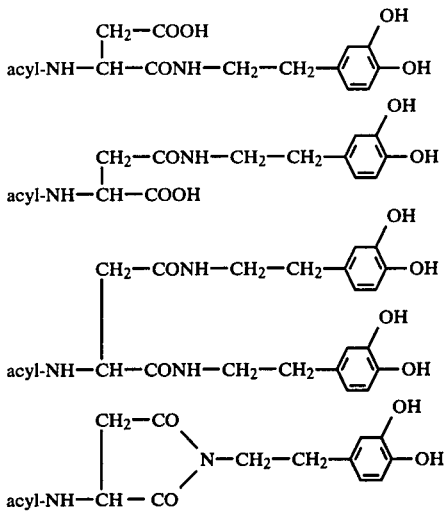

THE CARBOXYL GROUP

In the form A and B the carboxyl group which is not bonded to amine, may be present
(a) as free carboxylic acid group of the formula —COOH
(b) as an ester group of the formula —COOC$_p$H$_{2p+1}$, wherein p is 1 or 2
(c) as an amide group of the formula —CONHR', wherein R'=H or lower alkyl (C$_{1-4}$)
(d) as quaternary ammonium salt of the formula —COO$^-$+NH(R')$_3$, wherein R'=H or lower alkyl (C$_{1-4}$).

THE ACYL GROUP

The acyl group attached to the amino group in the aspartic acid moiety in the desired final product has the formula R"CO—, wherein R"=C$_x$H$_{2x+1}$ in which x=0–17, particularly 0 or 1.

THE STRUCTURE OF THE AMINE

The amine may be a compound within the group
(a) phenyl alkyl amines of the general structure

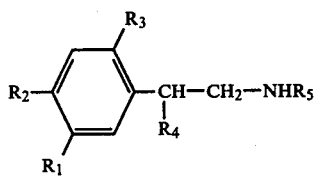

wherein
R$_1$=H, OH or OCH$_3$,
R$_2$, R$_3$, R$_4$=H or OH,
R$_5$=H or CH$_3$
(see examples of such in table I)
(b) indolyl alkyl amines of the general structure

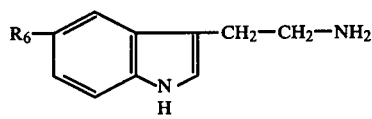

wherein
R$_6$=H, OH or OCH$_3$.
(examples of such, see table II)
(c) aliphatic amines of the general structure

R$_7$—CH$_2$—CH$_2$—NH$_2$ wherein
R$_7$=H, OH, CH$_2$—COOCH$_3$, CH$_2$—COOC$_2$H$_5$ or a sulphonic ester group (example: ethanol amine, taurine)
(d) piperidine

Table 1

Examples of phenyl alkylamines (a)

| Name | R$_1$ | R$_2$ | R$_3$ | R$_4$ | R$_5$ |
|---|---|---|---|---|---|
| dopamine (DA) | OH | OH | H | H | H |
| 2-phenyl ethyl amine | H | H | H | H | H |
| tyramine | H | OH | H | H | H |
| noradrenalin | OH | OH | H | OH | H |
| adrenalin | OH | OH | H | OH | CH$_3$ |
| normetanephrine | OCH$_3$ | OH | H | OH | H |
| octopamine | H | OH | H | OH | H |
| 6-OH-dopamine | OH | OH | OH | H | H |
| phenyl ethanol amine | H | H | H | OH | H |

Table 2

Examples of indole alkyl amines (b)

| Name | R$_6$ |
|---|---|
| serotonin | OH |
| tryptamine | H |
| 5-methoxytryptamine | OCH$_3$ |

2. The coupling products between the substituted aspartic acid and the biologically active amine can be prepared in several different ways.

2.1. In general, an activated form of the aspartic acid is reacted with an amine to an intermediate which may be protected on one of the carboxyl groups and/or on the amino group of the aspartic acid moiety. From this intermediate the possible protective groups are then removed, whereafter the desired product is obtained, possibly after acylation if the amino group of the aspartic acid moiety is made free in this process. The principles involved are described further in items 2.11–2.16.

2.11.
(a) The amino group in aspartic acid is protected during the synthesis with for instance a carbobenzoxy group (Cbz) or t-butoxycarbonyl (BoC), or
(b) the desired acyl group on the amino group of the aspartic acid is introduced before the acid or a derivative of the acid is reacted with the amine.

2.12 The carboxyl group of the aspartic acid which is not going to participate in the coupling with the amine, is protected, for instance with
(a) a group which is later to be removed (for example a benzyl group (Bzl) or a t-butyl group (t-Bu)), and after the coupling the carboxyl group is converted to a desired form, or
(b) a group which is to be maintained (for example as methyl- or ethyl ester or as amide).

2.13 The protected and/or acylated aspartic acid is reacted with the amine by
(a) using the acid in the form of an active ester, such as p-nitrophenyl, N-hydroxypiperidyl or N-hydroxysuccinimidyl ester
(b) using the acid in the form of a mixed anhydride, formed for instance with ethyl or t-butyl chloroformate (c) performing the reaction in the presence of a carbodiimide, such as N,N'-dycyclohexyl carbodiimide, possibly also in the presence of an activating reagent such as N-hydroxy succinimide (HOSu)

(d) using the acid in the form of an azide 2.14

(a) the amines which do not contain other funtional groups than the amino group, are used in their free form in the coupling mentioned in item 2.13

(b) the amines which also contain other functional groups, such as the hydroxy groups in dopamine, may either be used directly without protection of these groups or they can be protected with a suitable group.

2.15

(a) After the coupling the protective groups are split off from the amino group of the aspartic acid moiety (see 2.11) and also from the other carboxyl group (see 2.12) if the above forms of bonds A or B are desired (for instance Cbz and Bzl by catalytic hydrogenation, or BoC and t-Bu by treatment with weak acid), or (b) the protected coupling product is cyclized to imide from (D), for instance by subjecting it to a polar medium (methanol solution), possibly with light heating, or by careful treatment with acid or base, whereafter the possible protective group on the amino group is split off.

2.16 The amino group which has been made free, is acylated.

EXAMPLES OF PREPARATION

There are used purified and dried solvents of the types which are common in peptide chemistry (dimethyl formamide (DMF), methanol (MeOH), acetonitrile ($CH_3CN$), dioxan etc.). Abbreviations of the chemicals used: acetic anhydride ($Ac_2O$), triethylamine (TEA), ethanol (EtOH).

The course of reaction is usually followed by thin layer chromatography (TLC) in microscale (silica gel, mixtures of MeOH and chloroform ($CHCl_3$) development with iodine or UV-absorption). The stated yields expressed in percentages are calculated on basis of the starting material used in the step in question.

EXAMPLE 1

1. L-Aspartic acid β-benzyl ester (L-Asp-β-Bzl) (see 2.12a)

Lit: Can. J. Chem. 40, 570 572 (1962)

(L. Benoiton)

30 ml of concentrated sulphuric acid are added dropwise with stirring to 300 ml of dry ether, and 300 ml of benzyl alcohol are then slowly added.

The ether is evaporated off in vacuum and 39.6 g of L-aspartic acid are added in portions under stirring.

The solution is further stirred at room temperature for at least 24 hours, 600 ml of EtOH are added, and 150 ml of pyridine are then added dropwise under vigorous stirring.

The mixture is kept in a cold place over night, and the precipitated product is filtered off and washed well with ether.

The crude product (about 46 g) is recrystallized from 400 ml of water to which a few ml of pyridine have been added. Pure L-aspartic acid β-benzyl ester crystallizes as white, shiny flakes.

Melting point about 220° C.; Yield 27 g, 41%. Chromatographic purity is checked on silica gel TLC-plate in the system ethanol/$H_2O$:63/27. Developing agent: ninhydrin. $[\alpha]_D^{25} = +28.1°$ (c=1, 1 N HCl)

2. N-acetyl-L-aspartic acid β-benzyl ester (L-NAA-β-Bzl) (see 2.11b)

Prepared by three different methods:

(a) To a mixture of Asp-β-Bzl (33,3 g, 150 mmoles) and $Ac_2O$ (14,4 ml, 150 mmoles) in 400 ml DMF, TEA (46,2 ml, 330 mmoles) was added at room temperature. Asp-β-Bzl had a low solubility in DMF, while the formed NAA-β-Bzl dissolved. The reaction was discontinued after about 2 hours. The reaction mixture was then almost clear. Residues of Asp-β-Bzl were then filtered off, and the reaction mixture was evaporated to a yellow oil. This was dissolved in 1 N $NaHCO_3$ and the acidified (to pH 3) with a 1:1 mixture of conc. HCl:$H_2O$. Precipitated crystals were filtered off and dried. The yield of NAA-β-Bzl was 77% (30,5 g), melting point 110°–113° C. NMR (60 MHz acetone-$d_6$) δ: ~7,4 (s) 5H, 5,9–6,3 (m) 1H, 5,15 (s) 2H, 4,6–5,1 (m) 1H, 2,8–3,1 (d) 2H, 1,95 (s) 3H.

(b) A mixture of TEA (3,08 ml, 22 mmoles) and $Ac_2O$ (0,945 ml, 10 mmoles) was added to L-Asp-β-Bzl (2,23 ml, 10 mmoles) in DMF (25 ml). After stirring for 1 hr, TEA (0,5 ml, 0.3 mmoles) and $Ac_2O$ (0.5 ml, 0,5 mmoles) were added, resulting in a clear solution. The product could be isolated as its dicyclohexylamide (DCHA) salt according to one of the following two methods:

(1) The above solution was filtered, DCHA (2 ml, 10 mmoles) was added and the solution was standing at 4° C. overnight. After filtration and drying, 1,94 g (4,35 mmoles) of product was obtained. M.p. 188° C. $[\alpha]_D = +19.1°$ (c=182 mg in 10 ml EtOH).

(2) The above solution was filtered, DHCA (2 ml, 10 mmoles) and water (3 ml) was added and the mixture was standing at +4° C. overnight. After filtration and drying, 2,03 g (4,55 mmoles) of product was obtained. M.p. 189° C. $[\alpha]_D = +22,5°$ (c=192 mg in 10 ml of EtOH).

The reaction has been repeated in 0.1 mole scale, yielding 49% of a product having a m.p. of 188° C.

(c) 21 g (0,094 mole) L-Asp-β-benzyl were partly dissolved (slurried) in 50 ml of 2 N NaOH+40 ml $H_2O$. The mixture was cooled to 0° C. and placed in ice-water-bath. While stirring 11.2 ml (0.119 mole) acetic anhydride and 2 N NaOH were added dropwise simultaneously to the mixture so that pH was maintained at about 7.5. Towards the end of the dropwise addition the solution became water clear. (pH was controlled all the time by means of pH-meter with the electrodes immersed in the solution).

Reaction time: about 20 minutes.

The solution was then slowly heated to room temperature with continuous stirring (¾–1 hour). After filtration the solution was placed in an ice bath, and cold HCl (conc. HCl diluted with equal parts of $H_2O$) was added dropwise to pH 2 with continuous stirring. After standing in refrigerator overnight the oily precipitate had become crystalline. The crystals were isolated, washed with ice water, dried and weighed.

Appearance: Snow white, crystalline substance.

Mp. ~235° C. (not corrected)

$[\alpha]_D = +16°$ (c=1.6 g/100 ml solution EtOH corresponding to 5% MeOH)

Yield: 19.95 g (80%)

Chromatographically clear product (TLC CHCl$_3$-MeOH 9:1 or alcohol-water 63:37)

Comments: The mother liquor can be extracted with etyl acetate to increase the yield. The extracted product is treated as described under the purification procedure.

The product is usually sufficiently pure for further synthesis, but if necessary it may be purified by dissolving it in 1 N NaHCO$_3$, filtering the solution and reprecipitating the product by pH adjustment.

3. N-acetyl-aspartyl-α-dopamine β-benzyl ester (NAA-α-DA-β-Bzl)

This compound was prepared according to three alternative methods, a, b and c, of which a and b can be described as two step methods, while c can be described as a direct method.

a (see 2.13a)

Step I

N-acetyl-aspartic acid α-(p-nitro)phenyl-β-benzyl diester (NAA-α-ONP-β-Bzl)

At 0° C. 4.1 g of L-NAA-β-Bzl (15,4 mmoles) and 2.8 g of p-nitrophenol (20 mmoles) were mixed together in 70 ml of DMF. To this solution 4 g of dicyclohexyl carbodiimide (DCC) (18 mmoles) were added, and it was stirred for 5 hours. Precipitated dicyclohexyl urea (DCU) was filtered off, and the reaction mixture was evaporated on a rotavapor. This resulted in a yellow oil which solidified upon addition of about 10 ml of ether. The crystals were filtered off and recrystallized from EtOH to which some petroleum ether had been added. This yielded 3.2 g of NAA-α-ONP-β-Bzl (53%).

Melting point 112°–123° C.

Step II

Coupling with active ester to form NAA-α-DA-β-Bzl

A solution of 3-hydroxytyramine (dopamine, DA) in DMF was prepared by adding some DMF and TEA (3.8 ml, 22 mmoles) to the hydrochloride (3.8 g, 20 mmoles), the precipitated TEA.HCl was filtered off and the solution was diluted to 40 ml with DMF. This solution was added dropwise under a N$_2$-atmosphere at 0° C. to a solution of 7.7 g (20 mmoles) of NAA-α-ONP-β-Bzl in 60 ml DMF. The coupling reaction was followed by TLC and was complete after about 2 hours. The reaction mixture was evaporated and subjected to column chromatography (silica gel) with eluant mixtures of CHCl$_3$ and MeOH. This yielded 5.32 g (67%) of NAA-α-DA-β-Bzl.

Melting point 133°–135° C.

IR (KBr): 3370 (s), 3230 (s), 3070 (m), 1725 (s), 1660 (s), 1625 (s).

NMR (60 MHz, CDCl$_3$/CD$_3$OD) δ: ~7.3 (s) 5H, 6.4–6.9 (m) 3H, 5.1 (s) 2H, 4.3–4.9 (m) 5H, 3.2–3.5 (m) 2H, 2.4–2.9 (m) 4H, 1.9 (s) 3H.

MS 292, 157, 136, 123, 115, 108, 107, 91.

b (see 2.13a)

This method differs from Method a in that N-hydroxy-succinimide instead of p-nitrophenyl is used to activate the starting ester. By using N-hydroxy-succinimide as activator the optical activity of the starting material is maintained, whilst racemisation takes place when p-nitrophenyl is used.

Step I

N-acetyl-L-aspartic acid α-(N-hydroxy-succinimidyl)-β-benzyldiester (L-NAA-α-OSu-β-Bzl)

L-NAA-β-Bzl (530 mg, 2 mmoles) and N-hydroxy-succinimide (HOSu) (260 mg, 2.2 mmoles) were dissolved in THF (5 ml) and the solution was chilled to −20° C. (CCl$_4$/CO$_2$). At this temperature, a solution of DCC (455 mg, 2.2 mmoles) in THF (1 ml) was added under vigorous stirring. The reaction mixture was stirred for 2 hrs and then placed in the freezer overnight. The precipitated dicyclohexylurea (DCU) was filtered off and dried, and the melting point and weight of material were controlled (m.p. approx. 230° C., quantitatively).

Since the product would not crystallize easily, it was difficult to characterize further. Optical rotation of crude material (contaminated with some HOSu) $[\alpha]_D^{25} + 5.5°$ (c=236 mg/10 ml MeOH). R$_f$ 0.43 in CH$_2$Cl$_2$/MeOH (9:1).

Step II

N-acetyl-L-aspartyl α-dopamine β-benzyl ester (L-NAA-α-DA-β-Bzl)

The solution of L-NAA-α-OSu-β-Bzl (2 mmoles) in THF was chilled to −10° C., and a solution of dopamine (306 mg, 2 mmoles) in DMF (2 ml) was slowly added while stirring. After 90 min. at −10° C., the temperature was raised to room temperature and the solvent was evaporated in vacuo. The residue was dissolved in water (5 ml), and the product was extracted into CHCl$_3$ leaving HOSu and DA in the aqueous phase. After drying (MgSO$_4$) and evaporation of the solvent, the oily residue was dissolved in a small volume of MeOH and purified by column chromatography (Silicagel KG 60, 70–230 mesh, eluting solvent CHCl$_3$/MeOH (9:1)). The purified product had R$_f$ 0.41 (CH$_2$Cl$_2$/MeOH (9:1)) and $[\alpha]_D^{25} - 13.2°$ (c=224 mg/10 ml MeOH).

c (see 2.13c)

Chemical synthesis of N-acetyl-L-aspartyl-α-dopamine β-benzyl-ester (L-NAA-α-DA-β-Bzl) via in situ coupling with DCC and HOSu Dopamine was liberated from its hydrochloride salt by treating dopamine hydrochloride (949 mg, 5 mmoles) with TEA (0.84 ml, 5.2 mmoles) in a small volume of DMF and the precipitated TEA.HCl was filtered off. This solution was added to a mixture of L-NAA-β-Bzl (1.33 g, 5 mmoles) and HOSu (579 mg, 5 mmoles) in DMF (25 ml), and DCC (1.15 g, 5.5 mmoles) was added at 0° C. under N$_2$. After stirring for 1 hr at 0° C., the mixture was standing at 4° C. for several days before the precipitated material was filtered off and washed with 10% NaHCO$_3$ (3×10 ml), 0.1 N HCl (3×10 ml) and water (3×10 ml). After drying at 65° C., the crude product melted at 191° C.

4. Compounds prepared under 3. were converted to different desired final products (a) Cyclic form of N-acetyl-aspartyl-dopamine (c-NAA-DA)

A mixture of 1.8 g (4.5 mmoles) NAA-α-DA-β-Bzl (from 3., Method (a)) in 30 ml MeOH was, under N$_2$-atmosphere, treated with about 2 ml of 0.5 N NaOH.

After stirring at room temperature for 24 hours precipitated crystals were filtered off, yielding 1.1 g of cyclic imide (84%). The cyclic imide which was a product of the above type D, could be purified by column chromatography (silica gel).

Melting point 118°–120° C.
IR: 1775 (m), 1690 (s), 1650 (s), 1600 (m)

(b) Cyclic form of N-acetyl-L-aspartyl-dopamine (L-c-NAA-DA)

To L-NAA-$\alpha$-DA-$\beta$-Bzl (224 mg, 5.6 mmoles) (from 3., Method (b)) in MeOH (10 ml), a solution of NaOH (2 ml of 4·10$^{-3}$N) was added at $-13°$ C. The temperature was slowly raised to room temperature and the mixture stirred overnight. After evaporation of the solvent, the oily residue was dissolved in a small volume of MeOH and purified by column chromatography (Silicagel KG 60, 70–230 mesh, eluting solvent CHCl$_3$/MeOH (9:1)). The oily, purified product crystallized upon the addition of diethylether. The white crystals were dried in vacuum.

$[\alpha]_D^{25}$ $-3.7°$ (c=154 mg/10 ml DMF)
R$_f$ 0.32 in CH$_2$Cl$_2$/MeOH (20:3)
m.p. 190°–195° C.
NMR $\delta$: 6.6 (m) (DA), 1.96 (s) (acetyl).

(c) N-acetyl-aspartyl $\alpha$-dopamine (NAA-$\alpha$-DA)

NAA-$\alpha$-DA-$\beta$-Bzl (1 g, 2.5 mmoles) was dissolved in about 20 ml of MeOH and reduced by bubbling H$_2$-gas through the solution with 10% Pd/C catalyst. The hydrogenation was terminated after about 2 hours, and the reaction mixture was evaporated to dryness. This yielded 710 mg (97%) NAA-$\alpha$-DA, i.e. a product of the above type A.

Melting point 110° C. (decomp.)
IR: 1720 (s), 1650 (s), 1600 (s)

(d) N-acetyl-L-aspartyl $\alpha$-dopamine (L-NAA-$\alpha$-DA)

L-NAA-$\alpha$-DA-$\beta$-Bzl (376 mg, $\sim$10 mmoles) was dissolved in MeOH (20 ml), and a small amount of 10% Pd/C was added. Hydrogen gas was bubbled through the mixture for 1 hr. The catalyst was filtered off and the solvent was removed in vacuo. The product precipitated as a foamy material.

R$_f$ 0.18–0.24 in CH$_2$Cl$_2$/MeOH (20:3)
$[\alpha]_D^{25}$ $-27.8°$ (c=204 mg/10 ml MeOH)
NMR (CD$_3$OD) $\delta$: 6.5 (m) (DA), 1.95 (s) acetyl.

EXAMPLE 2

The methyl ester of the compound of 4. (d)

N-acetyl-L-aspartyl $\alpha$-dopamine-$\beta$-methylester (L-NAA-$\alpha$-DA-$\beta$-OMe)

Prepared by two different methods:

(a) L-NAA-$\alpha$-DA (616 mg, $\sim$2 mmoles) was dissolved in MeOH (5 ml) and the solution chilled to 0° C. SOCl$_2$ (146 $\mu$l, 2 mmoles) was added under vigorous stirring. After 2 hrs, the starting material had disappeared, and the solvent was removed in vacuo, leaving a white, foamy material. Purification by column chromatography (Silicagel KG 60, 70–230 mesh, eluting solvent CHCl$_3$/MeOH (9:1)) yielded 327 mg (50%) of a pale yellowish oily product.

R$_f$ 0.34–0.37 in CHCl$_3$/MeOH (20:3)
$[\alpha]_D^{25}$ $-22.2°$ (c=327 mg/10 ml MeOH)
NMR (CD$_3$OD) $\delta$: 6.5 (m) (DA), 3.63 (s) (OCH$_3$), 1.95 (s) (acetyl)

(b) L-NAA-$\alpha$-DA (377 mg, 1.22 mmoles) p-toluene sulphonic acid monohydrate (474 mg, about 2.5 mmoles) and methyl acetate (6 ml) were stirred at room temperature under N$_2$. L-NAA-$\alpha$-DA was not soluble in MeAc, but went slowly into solution after addition of the acid. The reaction mixture was stirred for 2 days, and was then washed with NaHCO$_3$ and H$_2$O. After drying the solvent was removed and the product was isolated as an oil. R$_f$=0.43 in MeOH:CH$_2$Cl$_2$ (15:85). Unreacted acid remained in the aqueous phase.

EXAMPLE 3

N-acetyl-L-aspartyl $\alpha,\beta$-didopamine (L-NAA-$\alpha,\beta$-(DA)$_2$)

This product, in which both carboxyl groups are bonded to a biologically active amine, was prepared by two different methods.

(a) Using a starting material in which one carboxyl group of the aspartic acid is already bonded to the amine.

Step I—Active ester L-NAA-$\alpha$-DA-$\beta$-OSu

To L-NAA-$\alpha$-DA (1.64 g, 5 mmoles) (from Example 1.4d) and HOSu (640 mg, 5.5 mmoles) in THF (25 ml) a solution of DCC (1.13 g, 5.5 mmoles) in THF (5 ml) was added at $-20°$ C. After 2 hrs, the precipitated DCU was filtered off, dried and checked for correct weight and melting point. The desired product had R$_f$ 0.34 in CHCl$_3$/MeOH (20:3).

Step II—Coupling with DA

The solution of L-NAA-$\alpha$-DA-$\beta$-OSu (5 mmoles) in THF was chilled to $-20°$ C., and a solution of DA (765 mg, 5 mmoles) in DMF (5 ml) was added. The reaction was almost completed after 4 hrs, but the stirring was still continued overnight at room temperature. After evaporation of the solvent in vacuo, the oily residue was purified by column chromatography (Silicagel KG 60, 70–230 mesh, eluting solvents CHCl$_3$ and mixtures of CHCl$_3$, MeOH and AcOH), yielding the desired product with R$_f$ 0.57–0.62 in CHCl$_3$/MeOH/AcOH (3:1:1).

NMR (CD$_3$OD) $\delta$=6.5 (m) (2DA), 1.98 (s) (acetyl)

(b) Coupling the amine to both of the carboxyl groups of the aspartic acid.

Step I—Active ester L-NAA-$\alpha,\beta$-(OSu)$_2$

L-NAA-$\beta$-Bzl (2.7 g, 10 mmoles) was dissolved in MeOH (15 ml), a small amount of 10% Pd/C was added, and hydrogen gas was bubbled through the mixture for 3 hrs. The catalyst was filtered off and the solvent was evaporated in vacuo. The crude product of L-NAA (2,04 g) was redissolved in THF (25 ml), and the solution was chilled to $-20°$ C. before the addition of HOSu (2.59 g, 22 mmoles) and DCC (4.84 g, 22 mmoles) in THF (10 ml). Following 2 hrs of stirring, the reaction mixture was left in the freezer overnight. Before use in the subsequent coupling reaction, the precipitated DCU was filtered off, dried and weighed, indicating a quantitative transformation.

Step II—Coupling with DA

L-NAA-$\alpha,\beta$-(OSu)$_2$ (9 mmoles) in THF was chilled to $-20°$ C., and DA (2.75 g, 18 mmoles) in DMF (10 ml) was added. The temperature was slowly raised to room temperature, at which the mixture was stirred overnight. After the addition of water (20 ml), the solvents were removed in vacuo, leaving a crude product consisting of three major components (shown by TLC on Silicagel, benzene:MeOH (1:1)) with $R_f$ 0.38, 0.56 and 0.69, the first being the main product of the desired structure. This component together with the component with $R_f$ 0.56 were isolated and purified by column chromatography on silicagel, using CHCl$_3$, benzene and MeOH as the eluting solvents. The desired product could be isolated by column chromatography and was shown to be identical to the product above, having an $R_f$ of 0.56 in the same TLC-system.

EXAMPLE 4

N-acetyl-L-asparaginyl α-dopamine (L-NAAsn-α-DA)

MeOH (25 ml) was saturated with ammonia gas (NH$_3$) at 0° C., and L-NAA-α-DA-β-Bzl (see Example 1.3 Method (b)) (833 mg, 2 mmoles) was added with stirring. The mixture was stirred overnight, the solvent evaporated in vacuo, and the crude product purified by column chromatography (Silicagel KG 60, 70-230 mesh, eluting solvent CHCl$_3$/MeOH (85:15)). 230 mg (30% yield) of pure product was isolated, having $R_f$ 0.1 on CHCl$_3$/MeOH (20:3).

NMR (CD$_3$OD) δ: 6.5 (m) (DA), 1.95 (s) (acetyl)

EXAMPLE 5

Chemical synthesis of the cyclic imide form for N-acetyl-L-aspartyl-serotonin via the N-hydroxy-succinimide (HOSu) activated ester method

Step I

N-acetyl-aspartyl-α-serotonin β-benzyl-ester (NAA-α-5HT-β-Bzl) which was prepared by two different methods.

(a) Serotonin oxalate (65 mg, 0.28 mmoles) was mixed with 116 mg (0.3 mmoles) NAA-α-ONP-β-Bzl (see Ex. 1, 3. a, step I) in 4 ml of DMF. Under N$_2$ atmosphere slightly more than 0.05 ml of TEA (>0.3 mmoles) was added to this mixture. The reaction was followed on TLC and was completed after about 2 hours. The reaction mixture was evaporated and examined by MS. This gave the following characteristic ions: m/e=423, 315, 272, 265, 248, 175, 159, 146, 108, 107, 91.

(b) DCC (455 mg, 2.2 mmoles) in 1 ml THF was added dropwise to a solution of L-NAA-β-Bzl (530 mg, 2 mmoles) and HOSu (260 mg, 2.2 mmoles) in 5.5 ml THF at −20° C., and the mixture was vigorously stirred for 2 hrs and then left overnight at −20° C. DCU was removed by filtration and a mixture of serotonin oxalate (538 mg, 2 mmoles) and TEA (0.28 ml, 2 mmoles) in DMF was added to the solution at −10° C. The reaction was almost completed after 3 hrs, but the mixture was stirred further overnight at room temperature. Distilled water (5 ml) was then added and the resulting mixture was extracted with CHCl$_3$.

Following evaporation of the solvent, the oily residue was chromatographed on a silicagel column (Silicagel KG 60, 70-230 mesh) using CHCl$_3$ and a mixture of CHCl$_3$ and MeOH as eluting solvents. The product was isolated by elution with CHCl$_3$:MeOH (9:1). $R_f$ 0.34 in TLC (silicagel), CH$_2$Cl$_2$:MeOH (9:1)).

Step II

Cyclization of L-NAA-α-5HT-β-Bzl to the cyclic imide form

L-NAA-α-5HT-β-Bzl (approx. 2 mmoles) was dissolved in MeOH (10 ml), and NaOH (4.25·10$^{-2}$ mmoles) was added. After 24 hrs, another batch of NaOH (4.25·10$^{-2}$ mmoles) was added. The reaction was completed after 3 days at room temperature. After evaporation of the solvent in vacuo, the residue was purified by column chromatography (Silicagel KG 60, 70-230 mesh), using CHCl$_3$ and mixtures of CHCl$_3$ and MeOH as the eluting solvents. The product was eluted with CHCl$_3$:MeOH (9:1). Yield 261 mg oily material $R_f$ 0.25 (TLC, silicagel, CH$_2$Cl$_2$:MeOH (9:1)) which was purified by preparative TLC NMR (CD$_3$OD) δ: 6.83 (m) (serotonin), 1.88 (s) (acetyl)

EXAMPLE 6

1. N-acetyl-L-aspartic α-piperidyl-β-benzyl ester (L-NAA-α-Pip-β-Bzl)

L-NAA-α-OSu-β-Bzl (5 mmoles) in THF (15 ml) was chilled to −20° C. and freshly distilled piperidine (5 ml) was added. After stirring for several hours, the mixture was allowed to warm up and stirred overnight at room temperature. To complete the reaction, the stirring was continued for 24 hrs more before the solvent was removed in vacuo. About 1 g of the crude product was purified by column chromatography (Silicagel KG 60, 70-230 mesh, eluting solvent CH$_2$Cl$_2$/MeOH (4:1). 238 mg (20% yield) of pure product was isolated, having $R_f$ 0.50 in CH$_2$Cl$_2$/MeOH (20:3).

$[\alpha]_D^{20} = -72°$ (c=239 mg/10 ml MeOH)

NMR (CD$_3$OD) δ: 7.3 (s) (phenyl), 5.06 (s) (CH$_2$), 1.9 (s) (acetyl), 1.58 (s) (piperidyl)

2. N-acetyl-L-aspartic α-piperidine (L-NAA-α-Pip)

The crude product from 1 was dissolved in MeOH (15 ml) and a small amount of 10% Pd/C and a few drops of AcOH were added before hydrogen gas was bubbled through the mixtue. After the reaction was completed, the catalyst was filtered off and the desired product could be isolated as a yellowish oil.

EXAMPLE 7

1. N-formyl-L-aspartic β-benzyl ester (L-NFA-β-Bzl)

The compound was synthesized according to a published procedure (Bull. Chem. Soc. Jap. 39, 391 (1966)) in 65 mmoles scale $[\alpha]_D^{25} + 25.3°$ (c=304 mg/10 ml MeOH) (lit. +28.6° in EtOH)

M.p. 122.5° C. (lit. 122°-125° C.)

2. N-formyl-L-aspartic α-dopamine-β-benzyl ester (L-NFA-α-DA-β-Bzl)

L-NFA-β-Bzl (2.50 g, 10 mmoles) and HOSu (1.3 g, 11 mmoles) were dissolved in 20 ml THF and cooled to −20° C. DCC (2.28 g, 11 mmoles) dissolved in 5 ml THF was added dropwise to the reaction flask with vigorous stirring. The reaction flask was maintained at −20° C. over night. Precipitated DCU was filtered off and the temperature was kept at −20° C. DA.HCl (1.17 g, 6.2 mmoles) was slurried in 5 ml DMF and DA was liberated with TEA (0.86 ml, 6.2 mmoles). This was charged dropwise to the reaction flask, and the temperature was gradually raised to room temperature. Stirring overnight. The solvent was removed on a rotavapor, and the residue was slurried in 10 ml water and extracted with 3×3 ml CHCl$_3$. The organic phase was dried with Na$_2$SO$_4$ and the solvent was evaporated off on a rotavapor.

R$_f$(CH$_2$Cl$_2$:CH$_3$OH=9:1) 0.35–0.40 main product
R$_f$(CH$_2$Cl$_2$:CH$_3$OH=9:1) 0.46 by product
The product was not further purified.

3. Cyclic form of N-formyl-L-aspartyl-dopamine (L-c-NFA-DA)

To L-NFA-α-DA-β-Bzl (250 mg, 1 mmole) in THF, NaOH was added in several portions until about 3 equivalents had been added. TLC showed that the starting material had reacted. Insoluble material precipitated during the reaction, and after removal of the solvent, water was added until the precipitated material was dissolved. Water was then removed in vacuo, the residue was purified by column chromatography (Silicagel KG 60, 70–230 mesh, eluting solvent CH$_2$Cl$_2$/MeOH (4:1)). 180 mg of brownish product was isolated.

R$_f$ 0.27 in CH$_2$Cl$_2$/MeOH (20:3)
$[\alpha]_{365\ nm}^{25}$ +36° (180 mg/10 ml MeOH)

EXAMPLE 8

Synthesis of N-acetyl-aspartic β-dopamine (NAA-β-DA)

1. N-Carbobenzoxy-L-aspartic acid (L-N-Cbz-Asp(OH))

This compound was prepared according to published methods (Bergmann, M., and Zervas, L., Chem. Ber. 65, 1192 (1932) Hanby, W. F. et al. J. Chem. Soc. 1950, 3239)

Yield 80% (lit. 90%)
M.p. 110° C. (lit. 116° C.)
$[\alpha]_D^{25}$ +9.4° (c=218 mg/10 ml HOAc) (lit. +9.6°).

2. N-Carbobenzoxy-L-aspartic anhydride (L-N-Cbz-Asp anhyd.)

This compound was prepared according to published methods (Bergmann, M., and Zervas, L., Chem. Ber. 65, 1192 (1932), John, W. D., and Young, G. T., J. Chem. Soc. 1954, 2870).

Yield 70% (Lit. 78%)
M.p. 110° C. (Lit. 111° C.)
$[\alpha]_D^{25}$ −36.9° (c=331 mg/10 ml HOAc) (Lit. −39.8°).

3. N-Carbobenzoxy-L-aspartic α-(p-nitrobenzyl)-ester (L-N-Cbz-Asp-α-pNBzl)

This compound was prepared as its dicyclohexylamine salt according to a published method (Schröder, E., and Klieger, E., Ann. 673, 208 (1964))

Yield 68% (Lit. 85%), decomp. 152° C. (Lit. 153°–154° C.)
$[\alpha]_D^{25}$ −12.8° (c=208 mg/10 ml HOAc) (Lit. −11.7°).

Liberation of the free acid from its salt:
L-N-Cbz-Asp-α-pNBzl.DCHA (2.67 g) and 20% citric acid (10 ml) were mixed in EtOAc (12 ml) and stirred for 30 min. at room temperature. After evaporation, the product was obtained as solid material, melting at 115° C.
Yield 85–90%.

4. N-Carbobenzoxy-aspartic α-(p-nitrobenzyl)-ester β-dopamine (N-Cbz-Asp-α-pNBzl-β-DA)

To N-Cbz-Asp-α-pNBzl (402 mg, 1 mmole) and DA (1 mmole), liberated from DA.HCl (190 mg, 1 mmole) with TEA in DMF, DCC (227 mg, 1.1 mmoles) in DMf was added, and the mixture was stirred overnight. The precipitated DCU was filtered off and the solvent was evaporated in vacuo. The oily residue was dissolved in EtOAc, washed with H$_2$O, dried over Na$_2$SO$_4$ and the solvent evaporated.

R$_f$ 0.65 in C$_6$H$_6$/MeOH (1:1)
$[\alpha]_D^{25}$ −17° (c=51 mg/10 ml MeOH)

5. N-acetyl-aspartic β-dopaminyl (NAA-β-DA)

L-N-Cbz-Asp-α-pNBzl-β-DA (0.1 mmole) was dissolved in HOAc and Ac$_2$O (0.1 ml, ∼0.1 mmole) and a small amount of 10% Pd/C was added. Hydrogen gas was bubbled through the mixture for 2.5 hrs. Another portion of Ac$_2$O (0.1 ml) was then added and the mixture was stirred overnight. The catalyst was filtered off, the solvent evaporated and the residue dissolved in water. After washing with ether, the water was evaporated off, leaving a crystalline product.

R$_f$ 0.5 in C$_6$H$_6$/MeOH (1:1)
NMR (D$_2$O) δ: 2.0 (Ac)

EXAMPLE 9

Synthesis of N-Stearyl-aspartic-dopamine cyclic imide form (N-Stearyl-c-Asp-DA)

1. N-Carbobenzoxy-L-aspartic β-benzyl ester (L-N-Cbz-Asp-β-Bzl)

This compound was prepared according to published methods (Bergmann, M., et al., Chem. Ber. 66, 1288 (1933); Davey, J. M., et al., J. Chem. Soc. 1966, 555; Berger, A., and Katchalski, E., JACS 73, 4084 (1951); Bryant, P. M., et al., J. Chem. Soc. 1959, 3868)

Yield: 50% (Lit. 54%)
M.p. 105.5° C. (Lit. 107°–108° C.)
$[\alpha]_D^{25}$ +12.0° (c=260 mg/10 ml HOAc) (Lit. +11.7°)

2. N-Carbobenzoxy-aspartic α-dopaminyl-β-benzyl ester (N-Cbz-Asp-α-DA-β-Bzl)

N-Cbz-Asp-β-Bzl (1.79 g, 5 mmoles), HOSu (0.58 g, 5 mmoles), DCC (1.13 g, 5.5 mmoles) and DA (5 mmoles, from DA.HCl (0.95 g, 5 mmoles) treated with TEA) was stirred overnight in DMF. The mixture was filtered, the solvent evaporated, the residue redissolved in EtOAc and washed successively with H$_2$O, 1 N NaHCO$_3$ and H$_2$O. After drying over Na$_2$SO$_4$, the solvent was evaporated, leaving the desired product as an oil.

R$_f$ 0.56 in CH$_2$Cl$_2$/MeOH (20:3)

3. N-Carbobenzoxy-aspartyl-dopamine cyclic imide form (N-Cbz-c-Asp-DA)

The oily product from 2 was dissolved in MeOH (20 ml) and NaOH (0.8 ml 1 N) was added and the mixture stirred for 3 hrs. The reaction mixture was acidified and used without further purification in the next reaction.
R$_f$ 0.47 in CH$_2$Cl$_2$/MeOH (20:3).

4. Aspartyl-dopamine cyclic imide form (c-Asp-DA)

The MeOH-solution of 3 was added a few drops of HOAc and a small amount of 10% Pd/C and hydrogen gas was bubbled through for 3 hrs. The catalyst was filtered off, the solvent evaporated, the residue dissolved in H₂O, and the aqueous solution washed with ether. Removal of H₂O left an oily product.
$R_f$ 0.2 in CH₂Cl₂/MeOH (20:3)

5. N-Stearyl-aspartyl-dopamine cyclic imide form (N-Stearyl-c-Asp-DA)

Equimolar amounts of SOCl₂ and DMF are mixed at 0° C., stirred at room temperature for 30 min. and evaporated in vacuo. One equivalent of stearic acid in CHCl₃ is added dropwise to the solution of SOCl₂/DMF at 0° C. and then stirred for 1 hr. The solution is then used in the subsequent reaction. One equivalent of c-Asp-DA and two equivalents of TEA are dissolved in DMF, and the solution of acid chloride prepared above is then added. The mixture is stirred for 1 hr. at room temperature and the solvent evaporated. The product is precipitated by adding water.
$R_f$ 0.58 in CH₂Cl₂/MeOH (20:3)

EXAMPLE 10

Step I

N-acetyl-L-Aspartic α-propylamine-β-benzyl ester (L-NAA-α-propylamine-β-Bzl)

To a mixture of L-NAA-β-Bzl (1.33 g, 5 mmoles) and n-propylamine (0.41 ml, 5 mmoles) in EtOAc (10 ml), DCC (1.14 g, 5.5 mmoles) in EtOAc (3 ml) and HOSu (0.63 g, 5.5 mmoles) were added at −10° C. The mixture was stirred at this temperature for 3 hrs and then at room temperature overnight. The precipitated DCU was filtered off and the EtOAc solution was washed with H₂O, dried over Na₂SO₄ and the solvent evaporated. The solid product was washed with ether and dried.
M.p. 110° C.
$[\alpha]_D$ −32.6° (471 mg in 10 ml CHCl₃)
NMR (CDCl₃) δ: 7.35 (Bzl), 2.0 (acetyl).

Step II

N-Acetyl-aspartic α-propylamine (NAA-α-propylamine)

A suspension of NaH (0.3 mmole) in oil was washed thoroughly with petrol ether and added to dry THF. To this mixture, NAA-α-propylamine-β-Bzl in THF was added dropwise. The precipitated material was isolated and purified by column chromatography (Silicagel KG 60, eluting solvent CH₂Cl₂ and MeOH). The product was eluted with MeOH and shown to be the desired material by NMR.
NMR (CD₃OD) δ: 1.9 (Ac), 1.5 (CH₃—CH₂—)

EXAMPLE 11

Chemical synthesis of the cyclic imide form of N-acetyl-aspartic acid-noradrenalin (NAA-Nor) by the p-nitrophenyl (ONP) active ester method

1. Generation of NAA-α-Nor-β-Bzl

Noradrenalin (1 g, 5.9 mmoles) was added to a solution of NAA-α-ONP-β-Bzl (2.35 g, 6.1 mmoles) in DMF (70 ml) under N₂ at 0° C. While stirred, the mixture was slowly heated to a temperature of approximately 30° C. After 3 hrs, TLC showed that all of the ONP-ester had reacted. The mixture was left at +4° C. for 3 days and the solvent was evaporated. After purification by column chromatography, 1.63 g (67%) of the product was isolated.

2. Generation of the cyclic imide 0.1 N NaOH (0.2 ml) was added to a solution of NAA-α-Nor-β-Bzl (625 mg, 1.5 mmoles) in MeOH (5 ml). The mixture was stirred at room temperature for 30 min. at +4° C. for 24 hrs and then left at −20° C. for 3 days. After evaporation of the solvent, the crude mixture was chromatographed on a column. In this manner, 235 mg (26.5%) of crystalline pure product (checked by TLC) could be isolated.

It is realised that transport of certain drugs across the blood-brain barrier and into the brain in mammalian systems including man is difficult to achieve. In our approach to solve this problem, the potential drugs consist of two different parts, one being the "active principle", the other being a naturally occurring "carrier"-molecule. These two parts are linked together by a covalent chemical bond.

The resulting substance is capable of being transported across the blood-brain barrier to the desired site of action, where the covalent link between the two parts is split enzymatically, releasing the "active principle" where it is required. In this manner, the therapeutically active principle—which itself cannot pass the blood-brain barrier—can exert its effect within the brain, and since much smaller doses should be required compared to present drugs, side effects are likely to be minimized.

The substances worked on so far, are with a great deal of certainty, occurring in the mammalian brain at very low concentrations (are of biogenic nature). They are obtained synthetically by classical techniques and are crystalline compounds, suitable and of polar nature (soluble in alcohols or buffers).

The "active principles" belong to the naturally occurring group of monoamines and include amongst others dopamine, serotonin and noradrenalin.

The "carrier" molecule is aspartic acid being in one of several possible substituted forms. Since the "carrier" itself is also naturally occurring in the brain in fairly high concentrations, increased concentrations of this are expected to be of no great concern.

In the experimental program so far, we have given priority to certain important aspects. Within this, a number of different substances have been synthesized and characterized by instrumental chemical methods for the determination of important parameters like structure, purity, stability, solubility etc. Several of these substances have also been carried through biological tests (see below). The substances that up to now have been synthesized or are presently being worked on are the following:

Cyclic imide forms of N-acetyl-D,L-aspartic acid-amine, where the amine is dopamine, serotonin and noradrenalin
Cyclic imide forms of N-acetyl-L-aspartic acid-amine, where the amine is dopamine, serotonin and noradrenalin
N-acetyl-L-aspartyl-α-amine, where the amine is dopamine, serotonin and noradrenalin
N-acetyl-L-aspartyl-β-OMe-α-amine, where the amine is dopamine, serotonin and noradrenalin
N-acetyl-L-aspartyl-β-dopamine
N-acetyl-L-aspartyl-α,β-(dopamine)₂
The cyclic imide form of N-formyl-L-aspartyl-dopamine Several of the compounds listed above have been carried through the following types of biological tests:
A. Administration intraperitoneally of non-labelled material in rats and measurements of levels of the "active principle" i.e. the given amine, in selected area of the brain. Doses and times are varied and results are compared with control values.
B. Administration intraveneous of "hot" (radioactive) material in rats and measurements of labelled material found in several parts of the brain as well as in organs, blood and uring (metabolites).
C. Administration orally and measurements of levels of the compound itself and of possible metabolites in blood (serum). Doses have been high, times are varied and the results have been compared with control groups.

RESULTS AND DISCUSSION OF TEST A

Method: The substances are dissolved in a suitable solvent (water with 0.01% ethanol) and administered intraperitoneally in rats. After a given time the animals are decapitated and dissected, and selected parts of the brain are analysed for changes in the content of amines and enzymatic activities. Doses as well as times are varied in the experiments.

In order to exemplify biological effects, results from the testing of N-acetyl-D,L,aspartyl-dopamine are listed in the enclosed table. These biological data have been obtained using a racemic form of the amine-complex. More recent data using the L-form have shown that the increase in brain-dopamine can be significantly improved.

These encouraging data are in accordance with our theoretical expectations since in a mixture of the D,L-form, the D-form is inactive because of its poor penetration into brain. Using the D,L-form of the dopamine-complex, the triatal dopamine concentration rose by about 25%, while after the L-form, the rise was more than 50%. Experiments are presently in progress to further elucidate these important findings.

RESULTS AND DISCUSSION OF TEST C

Additional experiments have shown the amine 1-X which seems to be quite stable in gastric juice at body temperature, has a rather high LD-value as mice did not show any significant change in behaviour during a 3 hours period after intraperitoneal and peroral administration of the compound (Dose=~2 g/kg body weight). Further analyses of serum concentrations are presently being worked on.

The experimental data obtained indicated that the dopamine complex penetrates the blood-brain barrier under certain experimental conditions. The increases in dopamine (DA) concentration in brain are modest, but the results are in keeping with the rises one would expect from theoretical considerations.

On the basis of the results obtained so far, there are reasons to believe that the principle which is shown to work well with dopamine, will work also with other compounds, including those mentioned above. Consequently, said principle opens for new alternatives which will make it possible to administer certain drugs in a new and more efficient manner.

TABLE

| RESULTS OF BIOLOGICAL TESTING OF "AMIN 1-X" ACCORDING TO METHOD A | | | | | |
|---|---|---|---|---|---|
| Substance | Dose (mg/kg) | Time (min.) | Analysis for | Nos animals | Results |
| Amin 1-X | 50 | 60 | DA | 3 | 11.48 ± 0.982 μg/g |
| Control | Solvent | | | 3 | 9.37 ± 1.514 " |
| Dopamine | 50 | | | 3 | same as control |
| Amin 1-X | 50 | 60 | 5HT | 3 | 0.22 ± 0.012 μg/g |
| Control | Solvent | | | 3 | 0.25 ± 0.029 " |
| Amin 1-X | 50 | 60 | COMT | | 10-12% reduction in COMT activity |
| Amin 1-X | 50 | 60 | MAO | | Ca. 30% reduction in MAO activity |
| Amin 1-X | 10 | 60 | DA | 3 | 9.01 ± 2.12 μg/g |
| Control | Solvent | | | 3 | 8.90 ± 0.92 " |
| Amin 1-X | 50 | 60 | DA | 3 | 9.05 ± 0.921 μg/g |
| Control | | | | 3 | 6.85 ± 0.722 " |
| Amin 1-X | 150 | 60 | DA | 4 | 14.42 ± 1.052 μg/g |
| Control | | | | 3 | 10.51 ± 1.079 " |
| Amin 1-X | 50 | 45 | DA | 3 | 10.51 ± 0.891 μg/g |
| Control | | | | | 8.92 " |
| Amin 1-X | 50 | 60 | | 3 | 11.50 μg/g |
| Control | | | | | 9.37 " |
| Amin 1-X | 50 | 120 | | 3 | 10.05 μg/g |
| Control | | | | | 8.96 " |

Amin 1 = DA = Dopamine
X = N-acetyl-D,L-aspartyl (NAA)
5HT = Serotonin

It has been found that the compound of Example 1.4b (L-c-NAA-DA) enters the brain in much higher amounts than N-acetyl aspartic acid and dopamine separately after intraperitoneal injection. Thus, L-c-NAA-DA was found in an amount of 20% in the brain, while the two components were found in amounts of 1% only when injected individually.

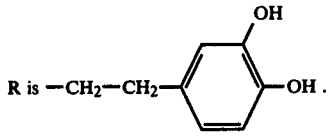

We claim:
1. Physiologically active compounds characterized in that they are coupling products of the formula

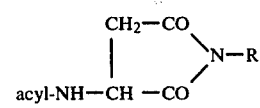

wherein "acyl" has the formula $C_xH_{2x+1}CO$ in which x is an integer from 0 to 17, and R is selected from the group consisting of the following formulas (a) and (b):

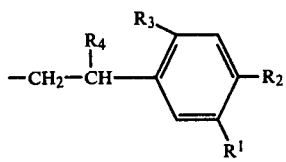 (a)

wherein $R_1$ is selected from the group consisting of H, OH and OCH$_3$, and $R_2$, $R_3$ and $R_4$ are each selected from the group consisting of H and OH, and —CH$_2$—CH$_2$—R$_7$ (b)

wherein $R_7$ is selected from the group consisting of H, OH, CH$_2$—COOCH$_3$, CH$_2$—COOC$_2$H$_5$ and a sulphonic ester group.

2. A compound of claim 1, characterized in that acyl is selected from the group consisting of formyl and acetyl.

3. A compound of claim 1, characterized in that it is a cyclic coupling product of dopamine and N-acetyl aspartic acid having the formula

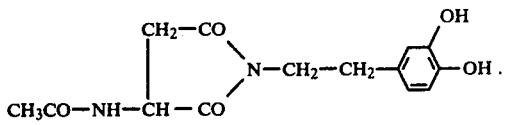

4. A compound of claim 1, characterized in that